US012138113B2

(12) United States Patent
Xu et al.

(10) Patent No.: US 12,138,113 B2
(45) Date of Patent: Nov. 12, 2024

(54) APPARATUS AND METHOD FOR DETECTING BONE FRACTURE

(71) Applicant: KONINKLIJKE PHILIPS N.V., Eindhoven (NL)

(72) Inventors: Jing Ping Xu, Shanghai (CN); Balasundar Iyyavu Raju, North Andover, MA (US); Anthony M. Gades, Snohomish, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 253 days.

(21) Appl. No.: 17/298,037

(22) PCT Filed: Nov. 28, 2019

(86) PCT No.: PCT/EP2019/083001
§ 371 (c)(1),
(2) Date: May 28, 2021

(87) PCT Pub. No.: WO2020/109519
PCT Pub. Date: Jun. 4, 2020

(65) Prior Publication Data
US 2022/0096047 A1   Mar. 31, 2022

(30) Foreign Application Priority Data

Nov. 30, 2018  (WO) ............... PCT/CN2018/118629
Jan. 15, 2019  (EP) ..................................... 19151811

(51) Int. Cl.
A61B 8/08        (2006.01)
A61B 8/00        (2006.01)

(52) U.S. Cl.
CPC ............ A61B 8/0875 (2013.01); A61B 8/085 (2013.01); A61B 8/469 (2013.01); A61B 8/54 (2013.01)

(58) Field of Classification Search
CPC ....... A61B 8/0875; A61B 8/085; A61B 8/469; A61B 8/54; A61B 8/08; A61B 5/4504
See application file for complete search history.

(56) References Cited

U.S. PATENT DOCUMENTS 4,798,210 A * 1/1989 Ledley ................. G01S 7/6245
                                                    348/42
5,426,684 A * 6/1995 Gaborski ................. G06T 5/40
                                                    706/924

(Continued)

FOREIGN PATENT DOCUMENTS

CN      102293668 B       9/2013
WO      2010132874 A1    11/2010
WO      WO-2017042304 A1 * 3/2017 ......... G01S 15/8952

OTHER PUBLICATIONS

International Search Report and Written Opinion of PCT/EP2019/083001, dated Jan. 15, 2020.

(Continued)

Primary Examiner — Baisakhi Roy
Assistant Examiner — Kaitlyn E Sebastian

(57) ABSTRACT

The present invention proposes an apparatus (120) and method for detecting bone fracture of a subject on basis of ultrasound images. The apparatus (120) comprises a first fracture detector (122) and a second fracture detector (124). The first fracture detector (122) is configured to receive a first ultrasound image of a region of the subject, to identify a bone in the first ultrasound image, to identify at least one focus area within the region on basis of the identified bone, to generate focus area information indicating position of the at least one focus area, and to instruct an acquisition of a second ultrasound image of the region acquired based on the generated focus area information. The second fracture detector (124) is configured to receive the second ultrasound image, and to detect bone fracture on the basis of the second (Continued)

ultrasound image. The second ultrasound image has a higher resolution in the at least one focus area than in the rest of the region, and the resolution of the at least one focus area in the second ultrasound image is higher than the resolution of the at least one focus area in the first ultrasound image.

18 Claims, 7 Drawing Sheets

(56) References Cited

U.S. PATENT DOCUMENTS

| | | | | |
|---|---|---|---|---|
| 2006/0189869 | A1* | 8/2006 | Sela | G01S 15/8993 600/443 |
| 2007/0043290 | A1* | 2/2007 | Goepp | A61B 5/6843 600/437 |
| 2010/0081931 | A1* | 4/2010 | Destrempes | G06T 7/12 382/128 |
| 2013/0041259 | A1 | 2/2013 | Harks | |
| 2014/0058266 | A1* | 2/2014 | Call | A61B 8/4427 600/443 |
| 2014/0163375 | A1 | 6/2014 | Wasielewski | |
| 2015/0148675 | A1 | 5/2015 | Haupt | |
| 2017/0086788 | A1 | 3/2017 | Rosen | |

OTHER PUBLICATIONS

Nascimento, Luis et al "Computer-Aided Bone Fracture Identification based on Ultrasound Images", 2015 IEEE 4th Portuguese Meeting on Bioengineering.
Turk, Fien et al"Evaluation by Ultrasound of Traumatic Rib Fractures Missed by Radiography", Emergency Radiology, vol. 17, 2010, pp. 473-477.
Hacihaliloglu, I. et al "Automatic Bone Localiztion and Fracture Detection from Volumetric Ultrasound Images using 3-D Local Phase Features", Ultrasound in Medicine and Biology, vol. 38, 2012, pp. 128-144.
Haider, B. "Power Drive Circuits for Diagnostic Medical Ultrasound", Proceeding of the IEEE International Symposium On Power Semiconductor Devices And ICs, Jun. 2006.
Griffith, J.F. et al 'Sonography compared with radiography in revealing acute rib fractures', AJR, 1999, vol. 173:1603-1609.
Augat, P. et al, 'Imaging techniques for the assessment of fracture repair', Injury, 2014, vol. 45S: pp. S16-S22.
Bemelman, Michael, et al 'The role of minimally invasive plate osteosynthesis in rib fixation: A review', Korean Journal of Thoracic Cardiovascular Surgery, 2016, vol. 49: pp. 1-8.
Pishbin, Elham et al, 'Comparison of ultrasonography and radiography in diagnosis of rib fractures', Chinese Journal of Traumatology, 2017.
Yousefifard, Mahmoud et al 'Comparison of ultrasonography and radiography in detection of thoracic bone fractures: a systematic review and meta-analysis', Emergency, 2016, vol. 4, No. 2, pp. 55-64.
Marin, Jennifer R. et al, 'Pediatric emergency medicine point-of-care ultrasound: summary of the evidence', Critical Ultrasound Journal, 2016, vol. 8 (83 pages).
Hwang, Eun Gu et al Simple X-ray versus ultrasonography examination in blunt chest trauma: effective tools of accurate diagnosis and considerations for rib fractures, Journal of Exercise Rehabilitation, 2016, vol. 12: 637-641.
Chan, Stewart Siu-Wa, Emergency bedside ultrasound for the diagnosis of rib fractures, American Journal of Emergency Medicine, 2009, vol. 27:617-620.
Hussian, Mohammad Arafat et al Strain-initialized robust bone surface detection in 3-D Ultrasound, Ultrasound in Medicine and Biology, vol. 43, No. 3, pp. 648-661. 2017.
Berton, Florian et al Segmentation of the spinous process and its acoustic shadow in vertebral ultrasound mages', Computrs in Biology and Medicine, 2016, vol. 72: 201-211.
McLean, et.al, 'Ultrasound determination of chest wall thickness: implications for needle thoracostomy', American Journal of Emergency medicine, 2011, vol. 29:1173-1177.
Noble, J.A. 'Ultrasound image segmentation and tissue characterization', Proceedings of the Institution of Mechanical Engineers, Part H: Journal of Engineering in Medicine, 2010, vol. 224, pp. 307-316.

* cited by examiner

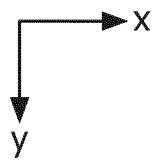
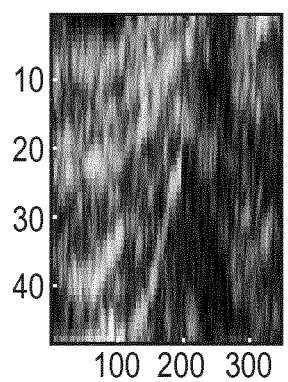
FIG. 7A
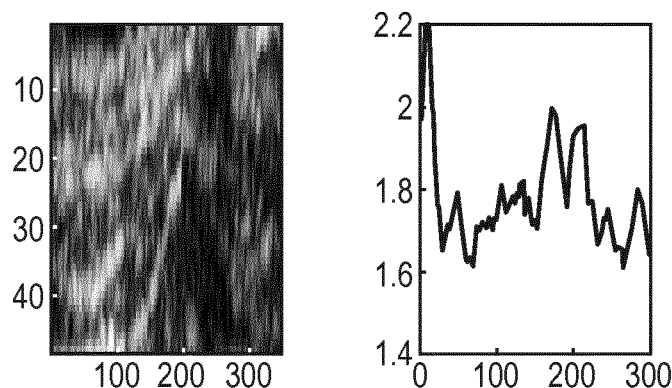
FIG. 7B
FIG. 7C
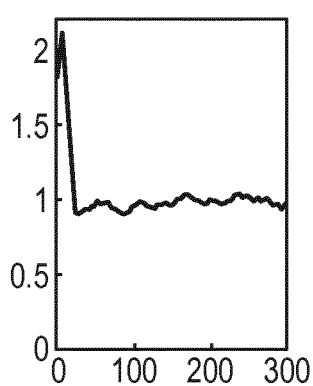
FIG. 7D
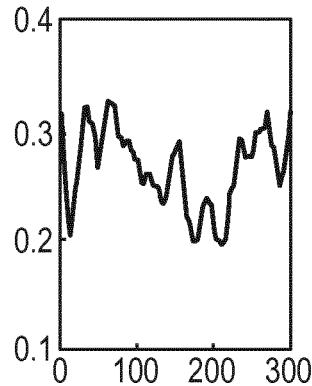
FIG. 7E
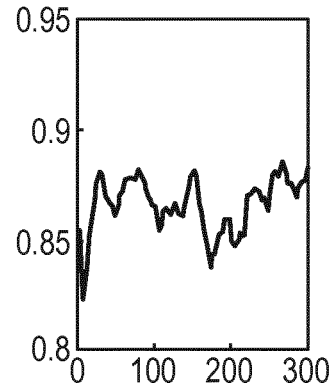
FIG. 7F

APPARATUS AND METHOD FOR DETECTING BONE FRACTURE

FIELD OF THE INVENTION

The present invention relates to ultrasound imaging, and more particularly to an apparatus and method for detecting bone fracture on the basis of ultrasound images.

BACKGROUND OF THE INVENTION

Bone fractures are quite common from traumatic injury (injuries from trauma). For example, rib fractures are the most common injuries resulting from blunt check(chest) trauma. There are several different approaches for diagnosis of bone fractures, including physical examination, conventional radiography such as diagnostic x-ray, advanced medical imaging modalities such as CT, MRI or SPECT (not often recommend for this task), and ultrasound imaging. Currently, physical examination and conventional radiography are the main diagnostic tools used in daily clinical practice, but cannot detect all bone fractures. For example, only around 49% of rib fractures are detected upon precise physical examination and conventional radiographs. CT and MRI can provide most detailed information of bone fractures, including localization, fragment dislocation and others. However, these more advanced medical imaging modalities are not always available at resource-limited situations such as prehospital and some small hospitals in developing countries, and they are not suitable for evaluating fracture reduction that needs repeated serial imaging during the whole treatment process.

Ultrasound imaging has been recognized as a good first-line alternative for the diagnosis of bone fractures in adults as well as especially children and pregnant women. Ultrasound imaging allows identification of the precise rib fracture location to help determine the site for surgical incision before rib fixation surgery which eliminates the potential for having to extend the incision. Ultrasound imaging has shown its advantages in pediatric fracture assessment owing to children's relative thinner chest wall (soft tissue) compared with that of adults. More advantages of ultrasound imaging include its portable, noninvasive and inexpensive cost-effective, as well as repeated examinations at bedside to evaluate fracture reduction during the whole treatment process.

However, the manual detection of bone fractures in ultrasound images is a highly operator-dependent, time-consuming process. It is always a challenging task for inexperienced users, especially when the examination time is critical. For example, the examination time for the whole chest of 12-paired ribs is preferably less than 12 minutes in emergency room, but shorter is better. In order to help physicians for quick identification of bone surface or hyperechoic line from the bone, some approaches using intensity and gradient information or morphologic features were proposed in automatic bone segmentation from ultrasound B-mode image. For example, I. Hacihaliloglu et.al. developed an approach for automatic bone localization and fracture detection using local phase features of 3D ultrasound data in "Automatic bone localization and fracture detection from volumetric ultrasound images using 3-D local phase features", published in Ultrasound in Medicine and Biology, 2012, Vol. 38:128-144. These existing approaches are complex in requirement of radiofrequency (RF) ultrasound signal and require high computation load in 3D local phase estimation. US 2007/043290 A1 disclosed a device for detecting bone fracture by comparing certain parameters of the waves reflected off of the bone to a threshold condition. "Computer aided bone fracture identification based on ultrasound image" by Lius Nascimento et al. proposed a 3-stage procedure for automatic identification of bone fracture. However, there is a need to further enhance the computer-aided bone fracture detection.

SUMMARY OF THE INVENTION

It would be advantageous to provide an improved approach for detecting bone fracture on the basis of ultrasound images.

In accordance with an embodiment of a first aspect of the present invention, there is proposed an apparatus for detecting bone fracture of a subject on the basis of ultrasound images. The apparatus comprises a first fracture detector configured to receive a first ultrasound image of a region of the subject and to identify a bone in the first ultrasound image. The first fracture detector is further configured to identify at least one focus area within the region on the basis of the identified bone, to generate focus area information indicating position of the at least one focus area, to instruct an acquisition of a second ultrasound image based on the generated focus area information. For example, the at least one focus area can comprise at least a portion of the identified bone. The apparatus further comprises a second fracture detector configured to receive the second ultrasound image and to detect bone fracture on the basis of the second ultrasound image, and the second ultrasound image is acquired based on the generated focus area information and has a higher resolution in the at least one focus area than in the rest of the region. The resolution of the at least one focus area in the second ultrasound image is higher than the resolution of the at least one focus area in the first ultrasound image.

In this way, the first ultrasound image is firstly used to identify a bone within the region, the at least one focus area is identified as one or more sub-regions of the region which is nearby the bone surface and covers at least a portion of the identified bone, and then the second ultrasound image is acquired in such a way that the resolution of the at least one focus area is higher than the rest of the region and the resolution of the at least one focus area in the second ultrasound image is higher than the resolution of the at least one focus area in the first ultrasound image, and is used to detect bone fracture. Ultrasound images having almost a fixed resolution across the imaged region are used for bone fracture detection in conventional approaches. Differently, in the approach proposed above, the second ultrasound image having higher axial and lateral resolutions in one or more sub-regions comprising the bone is acquired and used for bone fracture detection, and higher axial and lateral resolutions would result in a finer appearance of bone surface for more accurate detection. In other words, the first ultrasound image is firstly used to identify one or more focus areas, and the second ultrasound image is then acquired in such a way to zoom (high-resolution) in to the identified one or more focus areas. Thus, some fractures undetectable in the first ultrasound image, such as subtle fracture, can be detected on the basis of the second ultrasound image which has a high resolution.

In some embodiments, the second ultrasound image is acquired by performing additional signal processing on the first ultrasound image only in the at least one focus area. That is, the second ultrasound image is acquired by performing signal processing on the first ultrasound image without transmitting any additional ultrasound signals into the at least one focus area. Advanced signal processing can improve the image quality and/or the accuracy of the bone fracture detection at the cost of more computational time and or effort. Moreover, the larger the area to be processed, the more computational time or effort it will cost. Hence, it can reduce computational time and/or effort by performing additional signal processing only in the at least one focus area.

In accordance with some embodiments, the second ultrasound image is acquired by transmitting additional ultrasound beams at least toward the at least one focus area. In an embodiment, the first fracture detector is further configured to instruct an ultrasound image acquisition unit to acquire the second ultrasound image by transmitting additional ultrasound beams at least toward the at least one focus area, and the second fracture detector is further configured to receive the second ultrasound image acquired by the ultrasound image acquisition unit. The proposed apparatus can be communicatively connected to the ultrasound image acquisition unit, either directly or indirectly. The apparatus can send the generated focus area information to the ultrasound image acquisition unit, the ultrasound image acquisition unit can then acquire the second ultrasound image based on the received focus area information and send the acquired second ultrasound image to the apparatus, particularly to the second fracture detector of the apparatus.

In some embodiments, the first ultrasound image is acquired using a first ultrasound beam setting, the second ultrasound image is acquired using a second ultrasound beam setting at least in the at least one focus area, wherein the second ultrasound beam setting is different from the first ultrasound beam setting. The first fracture detection can be configured to instruct the ultrasound image acquisition unit to acquire the second ultrasound image using the second ultrasound setting at least in the at least one focus area. The second ultrasound beam setting may be different from the first ultrasound beam setting in various ways. In accordance with some embodiments, the first ultrasound beam setting and the second ultrasound beam setting are different in at least one of the following: (a) focal zone, (b) transmit frequency; (c) transmit pulse length; (d) steering angle.

In accordance with some embodiments, the first fracture detector is further configured to detect hematoma adjacent to the identified bone on the basis of the second ultrasound image, and the at least one focus area is generated on the basis of the detected hematoma. For example, the at least one focus area comprises at least a portion of the detected hematoma. For example, the at least one focus area can cover only the portion of the identified bone adjacent to which hematoma is detected, rather than covering all the identified bone. In this way, the at least one focus area can be even smaller. Generally, the smaller the at least focus area, the higher resolution of the at least one focus area in the second ultrasound image can be, and/or the less effort is required to acquire the same level of resolution for the at least one focus area. When bone fracture occurs, there is often hematoma present adjacent to the fracture. In ultrasound images, fresh hematoma appears like a hypoechoic pattern.

In accordance with some embodiments, the first fracture detector is further configured to detect bone fracture on the basis of the first ultrasound image. Although the resolution of the first ultrasound image is lower than that of the second ultrasound image at least in the at least one focus area, some bone fractures such as displaced fractures can be detected on the basis of the first ultrasound image.

In some particular embodiments, the first fracture detector is configured to firstly detect bone fracture on the basis of the first ultrasound image, and subsequently to identify the at least one focus area. In some further embodiments, the first fracture detector is configured to identify the at least one focus area if no bone fracture is detected by the first fracture detector on the basis of the first ultrasound image, and/or not to identify or detect the at least one focus area if bone fracture is detected by the first fracture detector on the basis of the first ultrasound image. In some further embodiments, the second fracture detector can be configured to receive the second ultrasound image of the region and to detect bone fracture on the basis of the second ultrasound image only if no bone fracture is detected by the first fracture detector on the basis of the first ultrasound image.

In this way, once a bone fracture is detected on the basis of the first ultrasound image, there is no need to acquire the second ultrasound image or to detect the bone fracture on the basis of the second ultrasound image. Sometimes, such as in emergency situations, it is more important to rule in fracture than to rule out fracture, or in other words, the detection of bone fracture can be stopped once at least one bone fracture (such as a major bone fracture) is detected. It is especially advantageous if a large area of the subject is to be scanned. For example, in the case of rib fracture detection, some or all of 12-pair ribs are to be examined.

In accordance with some embodiments, the apparatus further comprises a controller. The controller is configured to switch between a first detection mode and a second detection mode, and to control, in the first detection mode, an ultrasound image acquisition unit to acquire the first ultrasound image and to control, in the second detection mode, the ultrasound image acquisition unit, either to acquire the second ultrasound image or to acquire both the first and second ultrasound images.

In some embodiments, the controller is further configured to switch between the first detection mode and the second detection mode on the basis of a user input received from a user interface. The user input can be in various forms, including physical contact with the user interface (such as operating a physical button, touching a touch panel etc.) or contactless input (such as audio input, gesture input, etc.).

By allowing the switch between the first detection mode and the second detection mode, the apparatus can enable a more flexible detection mode or workflow to meet various situations. For example, the first detection mode might be applicable for time-urgent cases when a small bone fracture is not very critical, or in other words, when it is more important to detect a major bone fracture. For example, in some cases, the clinician may firstly use the first detection mode to do a fast, coarse exam, and then if needed, switch to the second detection mode to do a detailed detection. In some embodiments, in the first detection mode, the apparatus can be configured to present any detected bone and/or any identified focus area such as those comprising hematoma.

In accordance with some embodiments, the first fracture detector is further configured to receive a plurality of first ultrasound images acquired when an ultrasound transducer is moving relative to the subject, and first positional information on the ultrasound transducer relative to the subject corresponding to each of the plurality of first ultrasound images. The position information on the ultrasound transducer relative to the subject corresponding to particular first ultrasound images is the information about the position relative to the ultrasound transducer at which position the particular first ultrasound images is acquired. The first fracture detector is further configured to identify a bone, to detect the presence of a hematoma adjacent to the bone in each of the plurality of first ultrasound images, and identify a subset of the plurality of first ultrasound images in which the hematoma adjacent to the bone is present. The first fracture detector is further configured to generate second positional information on ultrasound transducer relative to the subject corresponding to each subset of the plurality of first ultrasound images. For example, the plurality of first ultrasound images are acquired when the ultrasound transducer is moved along the chest of the subject or along the ribs of the subject.

In some embodiments, a user interface is configured to present the second positional information.

In accordance with an embodiment of a second aspect of the present invention, there is proposed an ultrasound system for detecting a bone fracture of a subject. The ultrasound system comprises an ultrasound image acquisition unit comprising an ultrasound transducer, the above apparatus for detecting bone fracture coupled to the ultrasound image acquisition unit, and the ultrasound image acquisition unit is configured to acquire the first ultrasound image and the second ultrasound image. The ultrasound transducer is configured to transmit an ultrasound signal to a region of the subject and to receive an ultrasound echo signal from the region.

In accordance with an embodiment of a second aspect of the present invention, there is proposed a method of detecting bone fracture of a subject on the basis of ultrasound images. The method comprises steps of receiving a first ultrasound image of a region of the subject, identifying a bone in the first ultrasound image, and identifying at least one focus area within the region on the basis of the identified bone. For example, the at least one focus area comprises at least a portion of the identified bone. The method further comprises a step of instructing an acquisition of a second ultrasound image of the region and a step of receiving the acquired second ultrasound image, wherein the second ultrasound image has a higher resolution in the at least one focus area than in the rest of the region, and the resolution of the at least one focus area in the second ultrasound image is higher than the resolution of the at least one focus area in the first ultrasound image. The method further comprises a step of detecting a bone fracture on the basis of the second ultrasound image.

In accordance with an embodiment of a third aspect of the present invention, there is proposed a computer-readable medium comprising executable instructions, which when executed, cause a computer processor to perform the above method.

Other objects and advantages of the present invention will become more apparent and can be easily understood with reference to the description made in combination with the accompanying drawings.

DESCRIPTION OF THE DRAWINGS

The present invention will be described and explained hereinafter in more detail in combination with embodiments and with reference to the drawings, wherein:

FIG. 7A illustrates a sub-region selected from the ultrasound B-mode image of FIG. 3B; FIGS. 7B-7F illustrates five different texture analysis of the sub-region in FIG. 7A.

Figure 1:
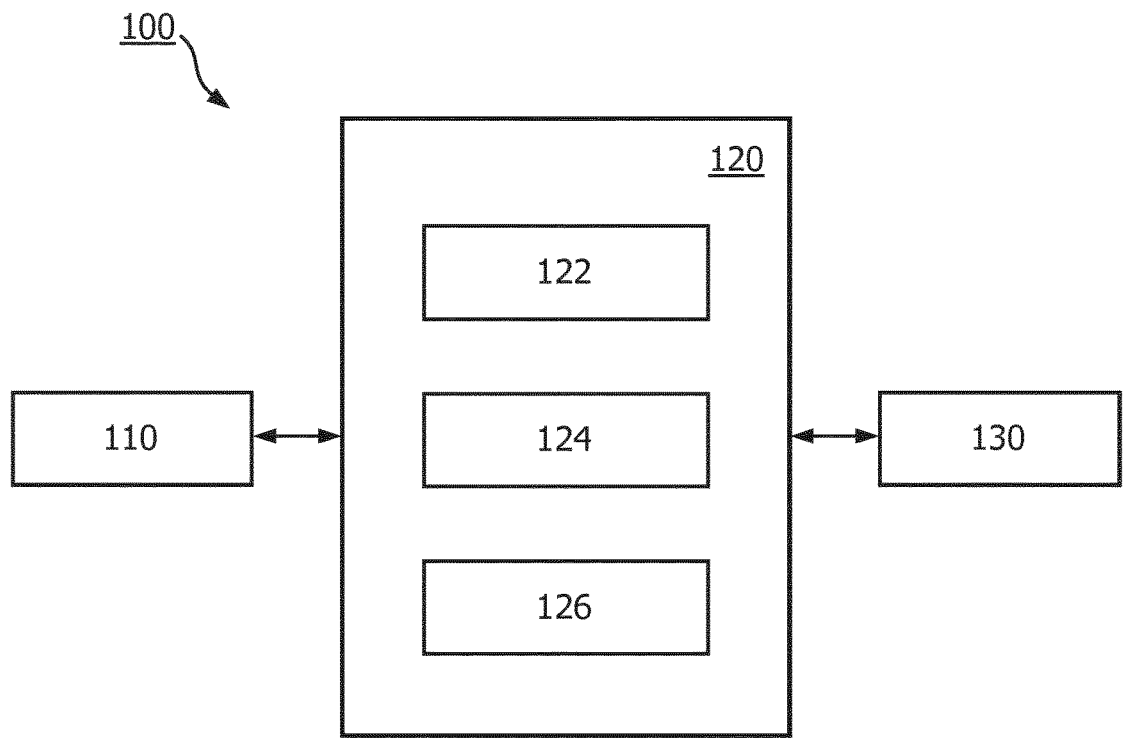
FIG. 1 illustrates an ultrasound system for detecting bone fracture of a subject in accordance with some embodiments of the present invention.

The same reference signs in the figures indicate similar or corresponding features and/or functionalities.

DETAILED DESCRIPTION

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn to scale for illustrative purposes.

Figure 2:
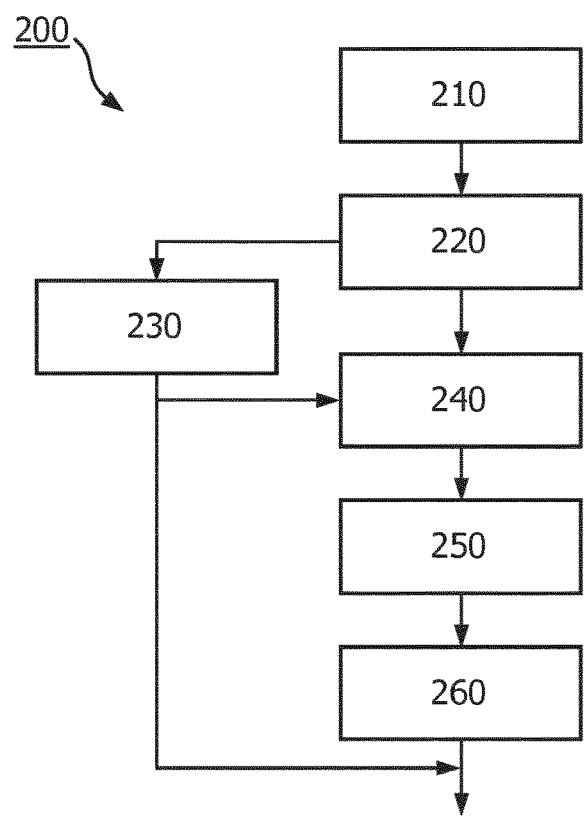
FIG. 2 illustrates a method of detecting bone fracture of a subject on basis of ultrasound images in accordance with some embodiments of the present invention.

FIG. 1 illustrates an ultrasound system 100 for detecting bone a fracture of a subject in accordance with some embodiments of the present invention. FIG. 2 illustrates a method 200 of detecting a bone fracture of a subject on the basis of ultrasound images in accordance with some embodiments of the present invention.

The ultrasound system 100 comprises an apparatus 120 for detecting a bone fracture of a subject, an ultrasound image acquisition unit 110, and a user interface 130. The ultrasound image acquisition unit 110 can be an ultrasound probe. The apparatus 120 is communicatively connected to the ultrasound image acquisition unit 110 and the user interface 130 in various ways, including wired or wireless connections, local or remote connections, etc. The user interface 130 may optionally be communicatively connected to the ultrasound image acquisition unit 110 as well. The apparatus 120, the ultrasound image acquisition unit 110, and the user interface 130 can be integrated into a single device, or can be physically separated from one or another. Each of the apparatus 120, the ultrasound image acquisition unit 110 and the user interface 130 can comprise one or more devices. In some embodiments, the ultrasound system 100 can comprise an ultrasound probe connectable to a computer system, and the computer system comprises a processor and a memory. For example, the computer system can be a personal computer, a smart phone, a tablet. The apparatus 120 comprises the processor and the memory of the computer system, wherein the memory comprises executable instructions, which when executed, cause the computer processor to perform the method 200. The user interface 130 can be part of the computer system as well or is connectable to the ultrasound probe and/or the computer system.

The ultrasound image acquisition unit 110 can be any kind of device that comprises an ultrasound transducer capable of transmitting and/or receiving ultrasound signals. For example, the ultrasound image acquisition unit 110 is configured to both transmit ultrasound signals toward a region of interest and receive echoes of the transmitted ultrasound signals from the region of interest. The ultrasound image acquisition unit 110 can be configured to acquire two dimensional (2D) or three dimensional (3D) ultrasound images. In some examples, the ultrasound transducer can comprise an array of transducer elements and thus be capable of scanning a 2D plane. In some examples, the ultrasound transducer can comprise a matrix of transducer elements and thus be capable of directly scanning a 3D volume. In some other examples, the ultrasound transducer comprises an array of transducer elements, the array of transducers is re-positioned and/or re-oriented to scanning multiple, different planes, either automatically or manually, and the two dimensional ultrasound data of multiple planes can be assembled into three dimensional ultrasound data of a volume of interest. For example, the ultrasound image acquisition unit 110 can comprise a mechanical three-dimensional ultrasound probe.

Typically, ultrasound echo signals received by the transducers will be beamformed, where the beamformed signals are processed by various signal processing, such as bandpass filtering, decimation, I and Q component separation, harmonic signal separation, speckle reduction, signal compounding, and/or noise elimination, and the processed signals can be further processed to obtain B-mode data, Doppler data, strain data, motion data, etc. Various ultrasound data can be further processed to form different kinds of ultrasound images. The signal and/or image processing can be performed by the same device, or by multiple devices. In some examples, an ultrasound probe can comprise the ultrasound transducer and one or more components configured to generate ultrasound images. In some examples, an ultrasound probe can comprise the ultrasound transducer and one or more components for performing some of the processing, and then a further device is configured to perform the rest to generate ultrasound images based on the output of the ultrasound probe. Such as device can be a standalone device, or can be part of a computer system.

As illustrated in FIG. 1, the apparatus 120 comprises a first fracture detector 122, a second fracture detector 124, and optionally, a controller 126.

The first fracture detector 122 is configured to receive a first ultrasound image of a region of the subject. The region of the subject is sometimes called imaged region here. The first ultrasound image can be a 2D image or a 3D image. The region of the subject can be a 2D plane of the subject, or a 3D volume of the subject.

The region of the subject can be pre-selected in accordance with pre-knowledge on the skeleton of the subject. The region of the subject can be selected as the region including the particular bone of interest in accordance with the pre-knowledge of the skeleton of the subject. For example, in cases that the subject is a human being, the region of the subject can be a part of the chest of the subject if the ribs are the bones of interest, or the region of the subject can be a part of the upper arm of the subject if the humerus is the bone of interest. In some embodiments, the first ultrasound image is acquired in accordance with one or more predetermined anatomical parameters of the subject. In this way, the first ultrasound image can be acquired by setting the focus zone at the depth of the bone of interest so as to enhance the resolution at that depth. For example, if the rib fracture of a human being is to be detected, the anatomical parameter comprises a parameter indicative the depth between the chest skin surface and the top of the rib. Such parameter can be determined as the chest wall thickness (CWT) minus a pre-determined value (such as 0.5 cm) indicative the typical distance between the pleural line and the rib for human beings. For example, the CWT can be a value determined on the basis of the body mass index or extracted from historical medical examinations such as a previously acquired ultrasound image of the particular people. Additionally or alternatively, several different acquisition modes can be automatically or manually selected on the basis of the CWT. For example, a penetration mode, in which the focus zone is set at a pre-determined large depth value, is selected for large CWT (such as 4~6.2 cm), a general mode, in which the focus zone is set at a pre-determined medium depth value, is selected for intermediate CWT (such as 2~4 cm), and a resolution, in which the focus zone is set at a pre-determined small depth value, can be selected for small CWT (such as 0.5~2 cm).

Figure 3:
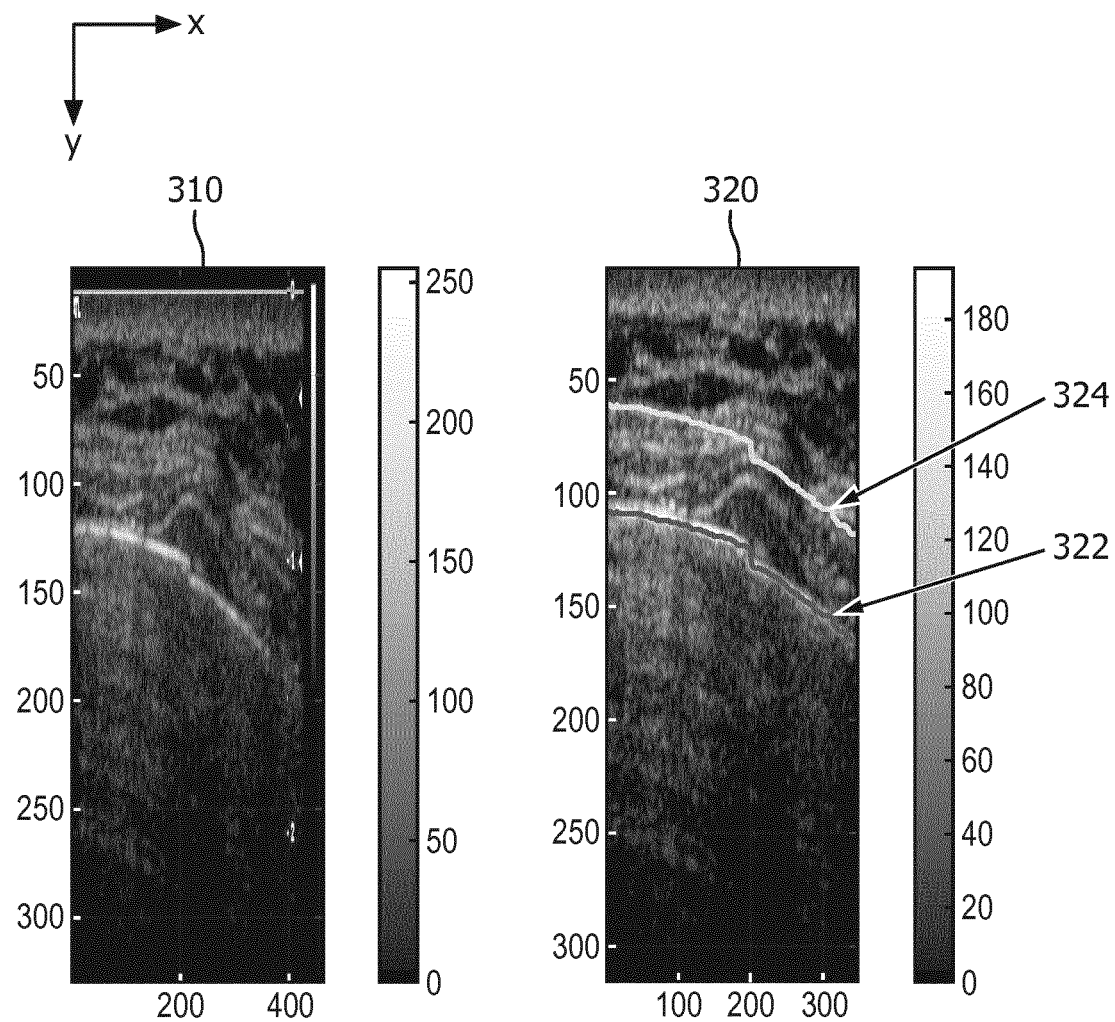
FIG. 3 illustrates two ultrasound B-mode images in accordance with some embodiments of the present invention.

The first fracture detector 122 is further configured to identify any bone in the received first ultrasound image. The identification of the bone can be implemented in any suitable ways, including those known or developed in future. In some embodiments, the identified bone can be presented to the user, e.g. via the user interface 130. For example, the first ultrasound image is displayed and the identified bone is delineated in the displayed first ultrasound image. Referring to FIG. 3, the ultrasound B-mode image 310 is an example of the first ultrasound image received by the first fracture detector 122. The ultrasound B-mode image 310 is the ultrasound B-mode image 310 overlaid with a solid line delineating the identified bone shown as curve 322. In FIG. 3, the y axis extends along the depth direction, and the x axis extends along the lateral direction.

In some embodiments, if no bone is identified by the first fracture detector 122, an alert signal can be generated. Additionally, the first fracture detector 122 may be configured to receive user input indicating a bone manually identified by the user, and/or user input assisting the bone detection, such as seed points, and to identify the bone on the basis of the user input. In an example, the user input can indicate one or more seed points and the first fracture detector 122 can be configured to identify a bone on the basis of the indicated seed points. In another example, the user input can indicate a spatial region, and the first fracture detector can be configured to identify a bone on the basis of the indicated spatial region. For example, the first fracture detector 122 can be configured to identify a bone within the spatial region, or to identify a bone with the spatial region and regions adjacent thereto.

Figure 4A:
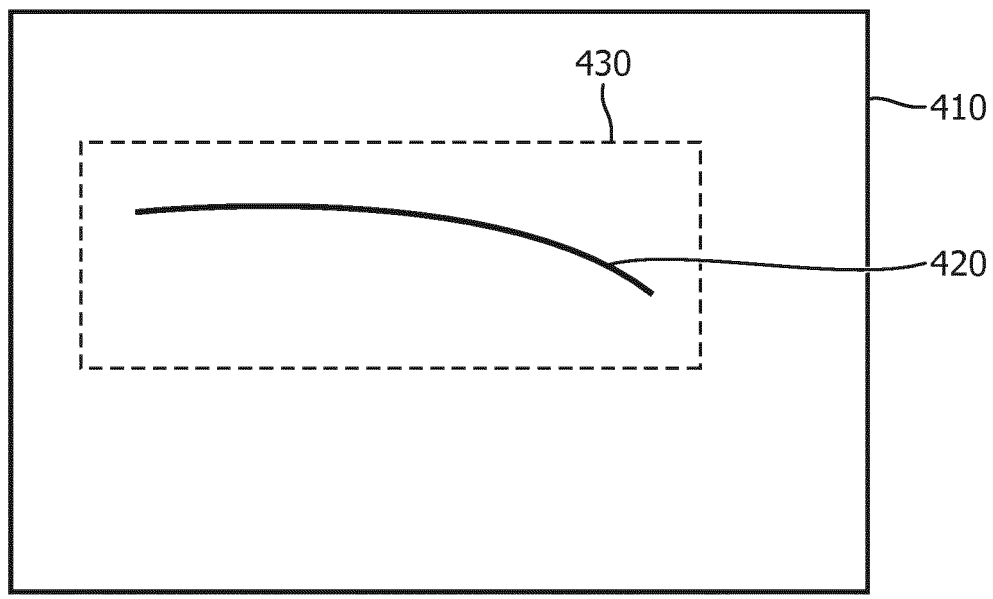
FIGS. 4A-4C illustrate the at least one focus area of an imaging area in accordance with different embodiments of the present invention.
Figure 4B:
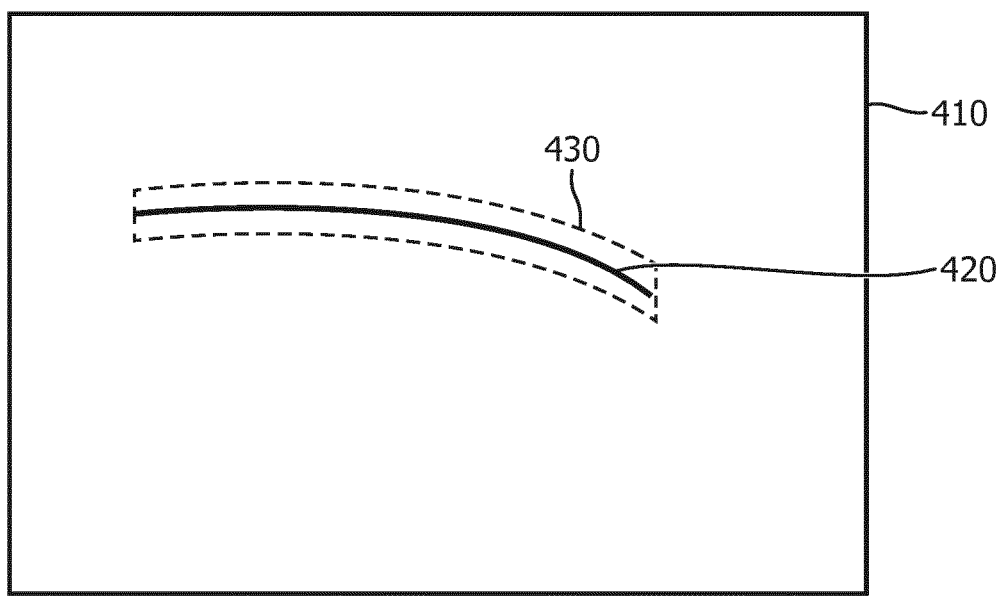
Figure 4C:
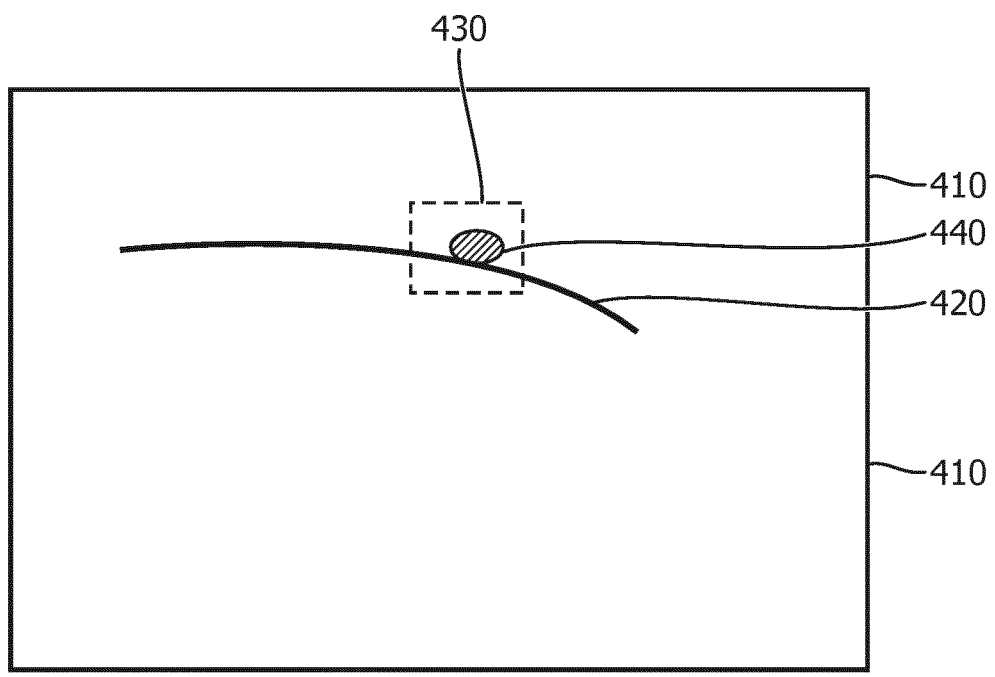

The first fracture detector 122 is further configured to identify at least one focus area within the region on the basis of the first ultrasound image, and to generate focus area information indicating position of the at least one focus area. The at least one focus area comprises at least a portion of the identified bone. FIGS. 4A-4C illustrate the at least one focus area of an imaging area in accordance with different embodiments of the present invention.

The at least one focus area can be any regular or irregular shape. For example, referring to FIG. 4A, the at least one focus area 430 can be a rectangular region including or covering the identified bone 420 in ultrasound image 410. For example, referring to FIG. 4B, the at least one focus area 430 can be a belt region centered at the identified bone 420. The focus area information can indicate the position of the at least one focus areas along at least one dimension. For example, the focus area information can indicate the depth of the at least one focus area, or the focus area information can indicate both the lateral position and the depth of the at least one focus area in a two-dimension imaged region.

In some embodiments, the first fracture detector 122 is further configured to detect hematoma adjacent to the identified bone on the basis of the detected hematoma. The at least one focus area can be so generated to include or cover the portion of the identified bone adjacent to the detected hematoma. For example, referring to FIG. 4C, a hematoma 440 is detected adjacent to the identified bone 420, and the at least one focus area 430 is identified as a region covering the hematoma 440 and the portion of the bone beneath the hematoma 440. For example, the at least one focus area may include the portion of the identified bone 420 whose distance to the detected hematoma is less than a predetermined threshold. Additionally, one or more focus areas can be defined by the user via the user interface, or in other words, the first fracture detector 122 can be further configured to receive user input indicative one or more focus areas and to identify the at least one focus area on the basis of the user input. In an example, the user input can indicate a spatial point, and the first fracture detector 122 can be configured to identify a focus area to be an area having a predetermined shape and size and centered at the spatial point indicated by the user input. In another example, the user input can indicate a spatial region by means of points, lines etc., and the first fracture detector 122 can be configured to identify a focus area based on the spatial region indicated by the user input, The identified focus area can be exactly corresponding to the indicated spatial region, or can be an area of a predetermined shape which covers the indicated spatial region.

The hematoma 440 adjacent to the bone 420 can be detected in any suitable way, for example by means of texture analysis. In some embodiments, a sub-region of the imaged region can be selected to perform the texture analysis. The sub-region can be a region above the identified bone. Here, the term "above" refers to be more superficial or shallow along the depth direction. Referring to the ultrasound image 320 in FIG. 3, the sub-region can be selected as the region between the two curves 322 and 324, where the curve 322 illustrates the identified bone, and the curve 324 is distanced away from the curve 322 by a predetermined value.

Texture analysis can comprise computing any of co-occurrence matrices and their properties such as correlation, entropy, contrast, energy, and homogeneity. Energy is defined as square sum of each matrix element, and reflects the grayscale distribution homogeneity of images and texture crudeness. Same values of all co-occurrence matrices resulted in small energy profiles; while high energy might be expected in case of unequal values among co-occurrence matrix values. Contrast reflects the sharpness of images and the depth of texture grooves. Deeper texture grooves are associated with high contrast and better visual sharpness, while low contrast are due to shallow grooves and blurred images. A higher number of pixels with high difference in grayscale (e.g. contrast profile) is associated with higher values of contrast. Entropy reflects the non-uniformity and complexity of image texture. Correlation reflects the consistency of image texture. Homogeneity reflects the homogeneity of image textures and scales the local changes of image texture. High values of homogeneity denote the absence of intra-regional changes and locally homogenous distribution in image textures.

FIG. 7A illustrates a region selected from the sub-region between the two curves 322 and 324 in ultrasound B-mode image 320 of FIG. 3B. FIGS. 7B-7F illustrate five different texture analyses of the region illustrated in FIG. 7A. In each of FIGS. 7B-7F, the x-axis represents the lateral direction, and the y-axis represents the amplitude of the corresponding texture property. The five texture properties are entropy in FIG. 7B, correlation in FIG. 7C, contrast in FIG. 7D, energy in FIG. 7E, and homogeneity in FIG. 7F.

It is known that a hematoma exists around the lateral position 200 on the x-axis. Referring to FIGS. 7B-7F, at least the entropy values in FIG. 7B, the energy values in FIG. 7E, and the homogeneity values in FIG. 7F show distinguishable changes around the lateral position 200 where the hematoma is located.

Analysis has shown that the entropy values are low for normal sub-periosteal soft tissue and high for the sub-periosteal hematoma. It can be noted that the user settings such as gain and TGC may affect some parameters (for examples: contrast and energy). However, these settings have less effect on parameters such as correlation and entropy. The entropy reflects the non-uniformity and complexity of image texture, and therefore, high entropy indicates more random texture within the image.

Several other features may also be used, for example: classical backscatter, echogenicity, attenuation coefficient, scattering parameters, parameters of amplitude or intensity histograms (e.g., Nakagami shape parameter), spectral features from Radio-frequency signal-based analysis, and motion features. Texture features for measuring speckle patterns are proposed to be used in our case since there are significant differences in ultrasound images for the normal sub-periosteal soft tissue and the sub-periosteal hematoma. Several research results have indicated that statistical texture analysis methods to be able characterize tissue properties well and provide complementary information to echogenicity.

The first fracture detector 122 is further configured to send out an instruction for acquiring a second ultrasound image of the region based on the generated focus area information, and the second fracture detector 124 is configured to receive the acquired second ultrasound image of the region, and to detect a bone fracture on the basis of the second ultrasound image. The second ultrasound image is acquired based on the generated focus area information, the second ultrasound image has a higher resolution in the at least one focus area than in the rest of the region, and the resolution of the at least one focus area in the second ultrasound image is higher than the resolution of the at least one focus area in the first ultrasound image. In some embodiments, the second fracture detector 124 can be configured to detect a bone fracture by combining the first and second ultrasound images.

The bone fracture can be detected in any suitable way. In some examples, the bone surface is firstly detected and then features, such as smoothness and continuity, of the detected bone are extracted. Furthermore, other features such as the detected hematoma, or texture features, strains of the tissues adjacent to the bone can be also used for detecting the bone fracture. In some examples, artificial intelligent based algorithm can be used to detect the bone fracture. Additionally or alternatively, the detection of the bone fracture can be assisted by one or more user inputs. For example, if the user detects a fracture by observing the ultrasound image, the user may indicate the location of the detected fracture via the user interface.

In accordance with some embodiments of the present invention, the second ultrasound image is acquired by performing additional signal processing on the first ultrasound image only in the at least one focus area. In some examples, the first fracture detector 122 can be configured to perform signal processing on the first ultrasound image to acquire the second ultrasound image by itself, or can be configured to instruct a further processing unit for performing signal processing to acquire the second ultrasound image. The first fracture detector 122 can send the generated focus area information to the further processing unit, and the further processing unit is configured to perform additional signal processing on the first ultrasound image only in the at least one focus area based on the generated focus area information. This further processing unit can be part of the apparatus 120 or can be communicatively connected to the apparatus 120.

In accordance with some embodiments of the present invention, the second ultrasound image is acquired by transmitting additional ultrasound beams at least toward the at least one focus area. The first fracture detector 122 can be communicatively connected to an ultrasound image acquisition unit 110, and can be configured to instruct the ultrasound image acquisition unit 110 to acquire the second ultrasound image by transmitting additional ultrasound beams at least toward the at least one focus area.

In some embodiments, the first ultrasound image is acquired using a first ultrasound beam setting, and the second ultrasound image is acquired using a second ultrasound beam setting at least in the at least one focus area, where the second ultrasound beam setting is different from the first ultrasound beam setting. The second ultrasound beam setting may be different from the first ultrasound beam setting in various ways. In accordance with some embodiments, the first ultrasound beam setting and the second ultrasound beam setting are different in at least one of the following: (a) focal zone, (b) transmit frequency; (c) transmit pulse length; (d) steering angle.

In an embodiment, the second ultrasound image is acquired by focusing the transmitted and/or receive ultrasound beams on the at least one focus area, e.g. on the depth of the at least one focus area. For example, the second ultrasound image is acquired by automatically setting the focal zone of the ultrasound beam to the at least one focus area.

Ultrasound focusing is a well-known technology. By means of this technology, the phased-array transducer is capable of adjusting the narrowest point in the ultrasound beam anywhere along its length. This is called the focal zone and it is typically within a 2-4 cm portion of the ultrasound beam that the highest resolution is achieved. Some existing ultrasound machines are able to effectively focus in multiple focal zones along the ultrasound beam, however, at the cost of affecting other factors such as frame rate since more than one scan or pulse is needed. More details of this technology can be referred to existing prior art such as "Power drive circuits for Diagnostic Medical Ultrasound" by B. Haider in Proceedings of the IEEE International Symposium on Power Semiconductor Devices and ICs, Jun. 4-8, 2006. Conventionally, the user can manually adjust the focal zone at various depths in order to see individual structures with the greatest clarity. Advantageously, in accordance with some embodiments of the present invention, the apparatus 120 is able to automatically identify at least one focus area and automatically set the focal zone at the at least one focus area without the need of user intervention. Hence, an ultrasound image with higher resolution at desired focus area can be acquired without the need of any user input.

In a further embodiment, in the second ultrasound beam setting, the transmit frequency can be increased and/or the transmit pulse length can be reduced so as to achieve a higher resolution.

In a further embodiment, in the second ultrasound beam setting, multiple steering angles can be used. Additionally, one or more steering angles can be dynamically decided. For example, one or more multiple steering angles can be decided on the basis of an orientation of the detected bone.

The first fracture detector 122 can be further configured to detect bone fracture on the basis of the first ultrasound image. Although the resolution of the first ultrasound image is lower than that of the second ultrasound image at least in the at least one focus area, some bone fractures such as a displaced fracture can be detected on the basis of the first ultrasound image.

Additionally, the controller 126 is configured to switch between a first detection mode and a second detection mode, and to control, in the first detection mode, the ultrasound image acquisition unit 110 to acquire the first ultrasound image and to control, in the second detection mode, the ultrasound image acquisition unit 110, either to acquire the second ultrasound image or to acquire both the first and second of ultrasound images. For example, the apparatus 120 can be configured to firstly operate in the first detection mode, and then to operate in the second detection mode. Since the second ultrasound image has a higher resolution than the first ultrasound image at least in the at least focus area, certain bone fractures that are not detectable in the first detection mode can be detected in the second detection mode. In some embodiments, in the second detection mode, the second ultrasound image is acquired based on the focus area information generated in the first detection mode. In some other embodiments, in the second detection mode, a first ultrasound image is firstly acquired to generate the focus area information and then a second ultrasound image is acquired based on the focus area information.

In some embodiments, the controller 126 is further configured to switch between the first detection mode and the second detection mode on the basis of a user input received from a user interface 130. For example, the user can firstly do a relatively coarse scanning by selecting the first detection mode, and then switch to a relatively fine scanning by selecting the second detection mode.

Referring to FIG. 2, the method 200 of detecting a bone fracture of a subject on the basis of ultrasound images is provided. In step 210, a first ultrasound image of a region of the subject is received. In step 220, a bone is identified in the first ultrasound image. In step 240, at least one focus area within the region is identified on the basis of the identified bone. In step 250, a second ultrasound image of the region is received, wherein the second ultrasound image has a higher resolution in the at least one focus area than in the rest of the region. In step 260, the bone fracture is detected on the basis of the second ultrasound image.

In some embodiments, in step 240, a hematoma adjacent to the identified bone is detected in the first ultrasound image, and the at least one focus area within the region can be identified on the basis of the detected hematoma.

In some further embodiments, the method 200 may further comprise a step 230. In step 230, bone fracture is detected on the basis of the first ultrasound image. The method 200 may continue in various ways after the step 230. In some embodiments, if no bone fracture is detected in step 230, the method 200 continues with step 240, and if a bone fracture is detected in step 230, the method 200 will skip the steps 240 to 260. For example, when it is used to rule in bone fracture, the detection can stop once any bone fracture is detected. In some other embodiments, the method 200 continues with step 240 no matter whether any bone fracture is detected in step 230 or not.

The field of view of an ultrasound transducer is normally smaller as compared to the region to be scanned or examined for bone fracture detection, and thus typically, the ultrasound transducer is swept across the region of interest, such as across the chest region when detecting a rib fracture.

Figure 5:
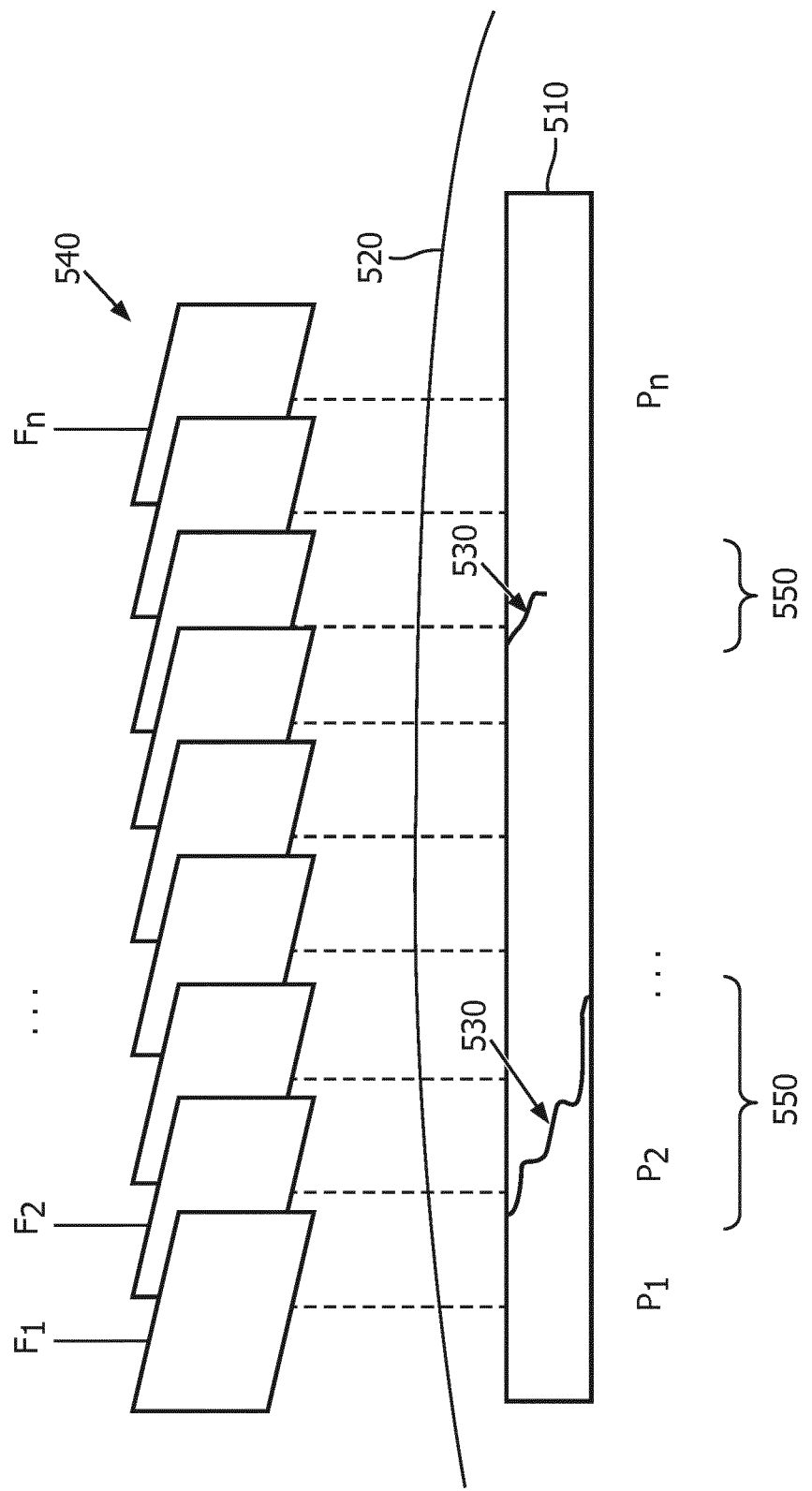
FIG. 5 illustrates a plurality of ultrasound images acquired when an ultrasound transducer is moving relative to a subject in accordance with some embodiments of the present invention.

FIG. 5 illustrates a plurality of ultrasound images 540 acquired when an ultrasound transducer is moving relative to a subject in accordance with some embodiments of the present invention. FIG. 5 illustrates a bone 510 with fractures 530 underneath the skin 520. A plurality of ultrasound images $F_1, \ldots, F_n$ is acquired at corresponding positions $P_1, \ldots, P_n$ when the ultrasound transducer is sweeping over a region of the subject. The movement of the ultrasound transducer relative to the subject can be directly controlled by a user. Alternatively, the ultrasound transducer can be connected to a driving device capable of moving the ultrasound transducer relative to the subject. The ultrasound transducer can freely sweep over the subject, and so the plurality of positions $P_1, \ldots, P_n$ where the ultrasound images are acquired can be any position, and two or more ultrasound images may be acquired at the same positon if the ultrasound transducer is kept at the same position for a while. These positions can be recorded by tracking the position of the ultrasound transducer in various ways, such as EM-sensors, motion sensor, acceleration sensor, etc.

In some embodiments, at each position, the method illustrated in FIG. 2 can be performed. For example, a first ultrasound image of a corresponding region of the subject is acquired, a bone is identified in the first ultrasound image, at least one focus area within the region is identified on the basis of the identified bone, a second ultrasound image of the region is then acquired, and then a bone fracture is detected on the basis of the second ultrasound image.

In accordance with some other embodiment of the present invention, the first fracture detector 122 is further configured to receive a plurality of first ultrasound images acquired when an ultrasound transducer is moving relative to the subject, and first positional information on the ultrasound transducer relative to the subject corresponding to each of the plurality of first ultrasound images. In other words, the first positional information of an ultrasound image $F_i$ indicates the corresponding position $P_i$. The first fracture detector 122 is further configured to identify a bone, to detect the presence of a hematoma adjacent to the bone in each of the plurality of first ultrasound images, and identify a subset 550 of the plurality of first ultrasound images in which the hematoma adjacent to the bone is present.

In some embodiments, the first fracture detector 122 can be further configured to detect a bone fracture, and different subsets of the plurality of first ultrasound images can be identified. For example, a first subset comprises first ultrasound images in which the bone fracture is detected, a second subset comprising first ultrasound images in which the bone fracture is not detected by the first fracture detector 122 but hematoma is detected.

The first fracture detector 122 is further configured to generate second positional information on ultrasound transducer relative to the subject corresponding to the subset of the plurality of first ultrasound images. Such second positional information can be presented via a user interface. Given such second positional information, the user may operate the ultrasound image acquisition unit 110 to scan one or more of those positions. In some examples, the user can trigger the apparatus 120 to switch from the first detection mode to the second detection mode, and to scan one or more of those positions in the second detection mode.

Figure 6:
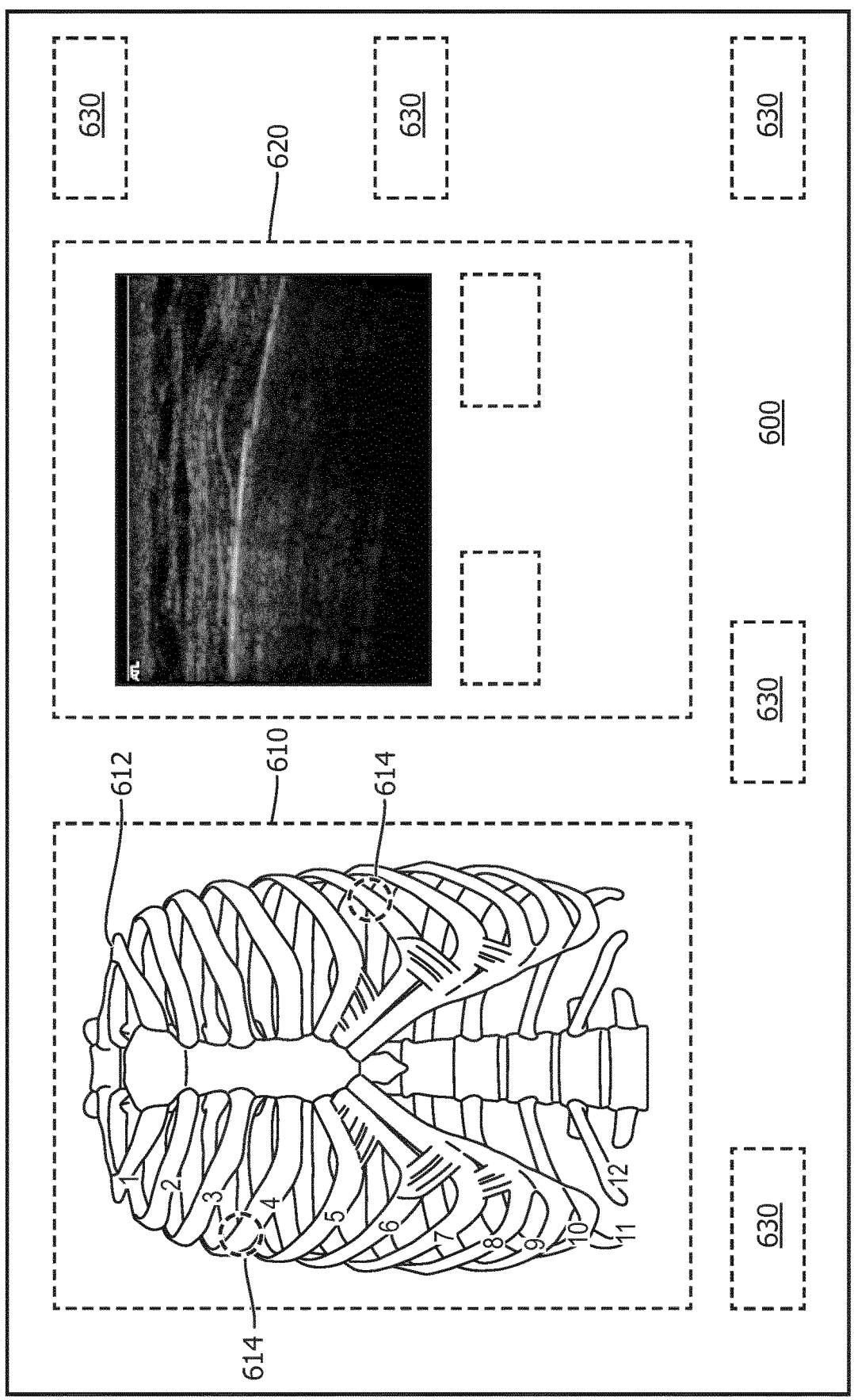
FIG. 6 illustrates a schematic view of a user interface in accordance with some embodiments of the present invention.

FIG. 6 illustrates an exemplary view 600 of a display of a user interface in accordance with some embodiments of the present invention. The view 600 may comprise a portion 610 which presents an image 612 of the bone(s) on which a bone fracture is to be detected, such as ribs as illustrated in FIG. 6. The image 612 can be a general anatomical model of the bones, or it can be an image of the bones of a particular subject such as a reconstructed 3D image from previously acquired CT, MR, or ultrasound images. In some embodiments, second positional information can be presented as markers 614 in the image 612. For example, whenever a bone fracture and/or a hematoma is detected in an ultrasound image, the position at which the ultrasound image is acquired is marked in the corresponding location in the image 612. Different markers can be used to respectively indicate bone fracture and hematoma. The view 600 may comprise a portion 620 which presents an ultrasound image. The ultrasound image can be a real-time image, or an ultrasound image previously acquired at a position selected by the user. In some examples, the detected bone fracture and/or the detected hematoma can be presented in the ultrasound image. The view 600 may comprise one or more additional portions 630 for presenting various information and/or receiving various user inputs. The sizes and the arrangements of the portions 610-630 are only for illustrative purposes. Any suitable size and arrangement can be implemented. In some embodiments, the view 600 can be dynamic and/or user-configurable.

The apparatus 120 can further comprise a reporting creator which is configured to record the detected bone fractures and/or the detected hematoma and optionally together with the position information, and generate a report on the basis of the recorded information. In some examples, the report can comprise one or more of the following information:

(a) whether there is any bone fracture detected;
(b) the number of the detected bone fractures;
(c) the positions of the detected bone fractures;
(d) whether there is any hematoma or abnormal soft tissue detected adjacent to the bone;
(e) suggestions for further actions, such as more advanced medical imaging like CT or repeated ultrasound examination if no bone fracture is detected but the subject is still in pain.

An exemplary workflow for detecting a rib fracture in accordance with an embodiment of the present invention will be described below.

1) The user selects a rib to start ultrasound scanning and marks that rib on either 3D CT chest image or 3D MRI chest image, or a 3D model of the chest;
2) A wideband linear ultrasound probe is used to determine the depth from the skin surface to the rib, and a specific setting is determined and set based on the depth for a specific subject;
3) The ultrasound probe is gently moved along the axis of rib (from the middle to side) to acquire a 2D ultrasound image sequence. The user may help rib identification by providing seed points for the rib surface detection. Alternatively, shadowing or loss of correlation below the suspected rib may be used for a more automated detection.
4) Rib properties (for example: any gap/step/smoothness) and echo-textures of sub-periosteal soft tissue (i.e. soft tissue adjacent to the bone) are extracted to determine if there are any gap/steps on the rib and/or any sub-periosteal hematoma (i.e. hematoma adjacent to the bone). If there are any ribs with gap/step/less smoothness, then the rib is considered as fractured; otherwise the rib could be normal or indeterminate. For example, if the bone surface is smooth and sub-periosteal soft tissue is normal, the rib is considered to be normal, or in other words no rib fracture. If the rib surface is smooth but the adjacent soft tissue looks like a hematoma or swelling from texture patterns, the rib fracture can be considered as indeterminate.

5) If the rib fracture is detected or indeterminate, the corresponding location is determined by means of the motion/positioning sensor capable of tracking the location of the ultrasound transducer, and then the ultrasound probe is gently moved to next rib;

6) If the rib is normal, then the ultrasound probe is gently moved along the axis of rib and events of (a) any gap/step/smoothness and (b) any sub-periosteal hematoma are checked until to the end side of the rib;

7) Repeat steps 4) to 6) until cover all the 12 paired ribs.

The technique processes described herein may be implemented by various means. For example, these techniques may be implemented in hardware, software, or a combination thereof. For a hardware implementation, the technical processes may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described herein, or a combination thereof. With software, implementation can be through modules (e.g., procedures, functions, and so on) that perform the functions described herein. The software codes may be stored in a volatile or non-volatile storage medium and executed by the processors.

Moreover, aspects of the claimed subject matter may be implemented as a method, apparatus, system, or article of manufacture using standard programming and/or engineering techniques to produce software, firmware, hardware, or any combination thereof to control a computer or computing components to implement various aspects of the claimed subject matter. The term "article of manufacture" as used herein is intended to encompass a computer program accessible from any computer-readable device, carrier, or media. For example, computer readable media can include but are not limited to magnetic storage devices (e.g., hard disk, floppy disk, magnetic strips . . . ), optical disks (e.g., compact disk (CD), digital versatile disk (DVD) . . . ), smart cards, and flash memory devices (e.g., card, stick, key drive . . . ). Of course, those skilled in the art will recognize that many modifications may be made to this configuration without departing from the scope or spirit of what is described herein.

As used in this application, the terms "detector" such as the first and second fracture detectors, "processor", "controller", are intended to refer to a general-purpose processor, a specific-purpose processor, a computer processor, or a computer-related entity, either hardware, a combination of hardware and software, software, or software in execution. For example, a component may be, but is not limited to, a process running on a processor, a processor, an object, an executable, a thread of execution, a program, and/or a computer. By way of illustration, both an application running on a server and the server can be a component. One or more components may reside within a process and/or thread of execution and a component may be localized on one computer and/or distributed among two or more computers.

What has been described above includes examples of one or more embodiments. It is, of course, not possible to describe every conceivable combination of components or methodologies for the purpose of describing the aforementioned embodiments, but one of ordinary skill in the art may recognize that many further combinations and permutations of various embodiments are possible. Accordingly, the described embodiments are intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

The invention claimed is:

1. An apparatus for detecting a bone fracture of a subject, the apparatus comprising:
   a first fracture detector configured to receive a first ultrasound image of a region of the subject wherein the first ultrasound image includes a bone of the subject, to identify the bone in the first ultrasound image, to detect a hematoma adjacent to the identified bone by performing texture analysis in a sub-region of the first ultrasound image, to identify at least one focus area within the region in the first ultrasound image as a region covering the hematoma and a portion of the identified bone adjacent to the hematoma, to generate focus area information indicating a position of the at least one focus area, and to instruct an acquisition of a second ultrasound image of the region based on the generated focus area information; and
   a second fracture detector configured to receive the second ultrasound image of the region, and to detect a bone fracture based on at least the second ultrasound image, wherein resolution of the second ultrasound image in the at least one focus area is higher than resolution of the second ultrasound image outside the at least one focus area within the region, and wherein the resolution of the second ultrasound image in the at least one focus area is higher than resolution of the first ultrasound image in the at least one focus area.

2. The apparatus of claim 1, wherein the first fracture detector is further configured to instruct an ultrasound image acquisition unit to acquire the second ultrasound image by transmitting additional ultrasound beams at least toward the at least one focus area, and the second fracture detector is further configured to receive the second ultrasound image from the ultrasound image acquisition unit.

3. The apparatus of claim 1, wherein the first fracture detector is further configured to instruct an ultrasound image acquisition unit to acquire the second ultrasound image using, at least in the at least one focus area, a second ultrasound beam setting different from a first ultrasound beam setting used to acquire the first ultrasound image, and wherein the first ultrasound beam setting and the second ultrasound beam setting are different in at least one of (a) transmit frequency; (b) transmit pulse length; (c) steering angle; or (d) focal zone.

4. The apparatus of claim 1, wherein the first fracture detector is further configured to attempt to detect the bone fracture based on the first ultrasound image, and wherein the second fracture detector detects the bone fracture only when the first fracture detector is unable to detect the bone fracture.

5. The apparatus of claim 1, further comprising:
   a controller configured to switch between a first detection mode and a second detection mode, and to control, in the first detection mode, an ultrasound image acquisition unit to acquire the first ultrasound image, and to control, in the second detection mode, the ultrasound image acquisition unit to acquire the second ultrasound image or to acquire both the first and second ultrasound images.

6. The apparatus of claim 5, wherein the controller is further configured to switch between the first detection mode and the second detection mode based on a user input received from a user interface.

7. The apparatus of claim 1, wherein the first fracture detector is further configured:
to receive a plurality of first ultrasound images acquired when an ultrasound transducer is moving relative to the subject, and first positional information on the ultrasound transducer relative to the subject corresponding to each of the plurality of first ultrasound images;
to identify the bone and to detect the hematoma within the sub-region adjacent to the bone in each of the plurality of first ultrasound images;
to identify a subset of the plurality of first ultrasound images in which the hematoma adjacent to the bone is present; and
to generate second positional information on the ultrasound transducer relative to the subject corresponding to each of the plurality of first ultrasound images in the subset.

8. An ultrasound system for detecting the bone fracture of the subject, the ultrasound system comprising:
an ultrasound probe comprising an ultrasound transducer configured to transmit an ultrasound signal to the region of the subject and to receive an ultrasound echo signal from the region; and
the apparatus of claim 1 coupled to the ultrasound probe, wherein the ultrasound probe is configured to acquire the first ultrasound image and the second ultrasound image.

9. A non-transitory computer readable medium storing instructions for detecting a bone fracture of a subject based on ultrasound images that, when executed by a computer processor, cause the computer processor to:
receive a first ultrasound image of a region of the subject, wherein the first ultrasound image includes a bone of the subject;
identify the bone in the first ultrasound image;
detect a hematoma adjacent to the identified bone by performing texture analysis in a sub-region of the first ultrasound image;
identify at least one focus area within the region in the first ultrasound image as a region covering the hematoma and a portion of the identified bone adjacent to the hematoma, and wherein performing the texture analysis includes computing a co-occurrence matrix and at least one of corresponding correlation, entropy, contrast, energy, or homogeneity properties;
initiate an acquisition of a second ultrasound image of the region, wherein resolution of the second ultrasound image in the at least one focus area is higher than resolution of the second ultrasound image outside the at least one focus area within the region, and wherein the resolution of the second ultrasound image in the at least one focus area is higher than resolution of the first ultrasound image in the at least one focus area;
receive the second ultrasound image; and
detect the bone fracture based on the at least one focus area of the second ultrasound image.

10. The computer readable medium of claim 9, wherein the second ultrasound image is acquired by an ultrasound probe transmitting additional ultrasound beams at least toward the at least one focus area.

11. An apparatus for detecting a bone fracture of a subject, the apparatus comprising:

a processor configured to receive ultrasound images of a subject; and
a non-transitory memory storing instructions that, when executed by the processor, cause the processor to:
receive a first ultrasound image of a region of the subject, wherein the first ultrasound image includes a bone of the subject;
identify the bone in the first ultrasound image;
detect a hematoma adjacent to the identified bone by performing texture analysis in a sub-region of the first ultrasound image;
identify at least one focus area within the region in the first ultrasound image as a region covering the hematoma and a portion of the identified bone adjacent to the hematoma;
generate focus area information indicating a position of the at least one focus area;
instruct an acquisition of a second ultrasound image of the region based on the generated focus area information, wherein resolution of the second ultrasound image in the at least one focus area is higher than resolution of the second ultrasound image outside the at least one focus area within the region, and wherein the resolution of the second ultrasound image in the at least one focus area is higher than resolution of the first ultrasound image in the at least one focus area; and
detect a bone fracture in the at least one focus area of the second ultrasound image.

12. The apparatus of claim 11, wherein the second ultrasound image is received from an ultrasound imaging probe that acquires the second ultrasound image by transmitting additional ultrasound beams at least toward the at least one focus area.

13. The apparatus of claim 11, wherein the second ultrasound image is received by the processor from an ultrasound imaging probe that acquires the second ultrasound image using, at least in the at least one focus area, a second ultrasound beam setting different from a first ultrasound beam setting used to acquire the first ultrasound image.

14. The apparatus of claim 13, wherein the second ultrasound beam setting is different from the first ultrasound beam setting with regard to at least one of transmit frequency, transmit pulse length, steering angle, or focal zone.

15. The apparatus of claim 11, wherein the instructions further cause the processor to switch between a first detection mode and a second detection mode, and to control at least one setting of an ultrasound imaging probe to acquire the first ultrasound image in the first detection mode, and to control the at least one setting of the ultrasound imaging probe to acquire the second ultrasound image in the second detection mode.

16. The apparatus of claim 11, wherein the at least one focus area has a predetermined shape and size centered at a spatial point indicated by a user input.

17. The apparatus of claim 1, wherein the sub-region is selected as a region between a first curve illustrating the identified bone and a second curve located a predetermined distance from the first curve.

18. The apparatus of claim 1, wherein the second fracture detector is further configured to detect the bone fracture by combining the first ultrasound image and the second ultrasound image.

* * * * *